(12) United States Patent
Sjostedt et al.

(10) Patent No.: US 8,091,226 B2
(45) Date of Patent: Jan. 10, 2012

(54) INTEGRATED HEADER CONNECTOR SYSTEM

(75) Inventors: Robbie J. Sjostedt, Foothill Ranch, CA (US); Farshid Dilmaghanian, Rancho Santa Margarita, CA (US); Jacques Naviaux, Rancho Palos Verdes, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 924 days.

(21) Appl. No.: 12/100,646

(22) Filed: Apr. 10, 2008

(65) Prior Publication Data

US 2008/0255631 A1    Oct. 16, 2008

Related U.S. Application Data

(60) Provisional application No. 60/911,161, filed on Apr. 11, 2007, provisional application No. 61/024,660, filed on Jan. 30, 2008.

(51) Int. Cl.
*H01R 43/20* (2006.01)

(52) U.S. Cl. .............. 29/876; 29/874; 29/881; 607/37

(58) Field of Classification Search .......... 29/825, 29/874, 876, 881; 607/37
See application file for complete search history.

(56) References Cited

U.S. PATENT DOCUMENTS

| | | |
|---|---|---|
| 4,072,154 A | 2/1978 | Anderson et al. |
| 4,105,037 A | 8/1978 | Richter et al. |
| 4,202,592 A | 5/1980 | Rullier et al. |
| 4,262,673 A | 4/1981 | Kinney et al. |
| 4,461,194 A | 7/1984 | Moore |
| 4,934,366 A | 6/1990 | Truex et al. |
| 5,012,807 A * | 5/1991 | Stutz, Jr. .............. 607/37 |
| 5,076,270 A * | 12/1991 | Stutz, Jr. .............. 607/37 |
| 5,413,595 A | 5/1995 | Stutz, Jr. |
| 5,817,984 A | 10/1998 | Taylor et al. |
| 5,866,851 A | 2/1999 | Taylor et al. |
| 6,029,277 A | 2/2000 | Picchione, II |
| 6,192,277 B1 | 2/2001 | Lim et al. |
| 6,428,368 B1 | 8/2002 | Hawkins et al. |
| 6,498,952 B2 | 12/2002 | Imani et al. |
| 6,671,544 B2 | 12/2003 | Baudino |
| 6,671,554 B2 | 12/2003 | Gibson et al. |
| 6,878,013 B1 | 4/2005 | Behan |

(Continued)

FOREIGN PATENT DOCUMENTS

WO    WO 00/64535 A1    11/2000

OTHER PUBLICATIONS

Preliminary Report completed and mailed Oct. 13, 2009 from corresponding PCT Application No. PCT/US2008/059924, filed Apr. 10, 2008 (8 pages).

(Continued)

*Primary Examiner* — Carl Arbes
(74) *Attorney, Agent, or Firm* — Klein, O'Neill & Singh, LLP

(57) ABSTRACT

Connector assemblies for use with implantable medical devices having easy to assemble contacts is disclosed. The connector assemblies are generally formed by coupling a plurality of contact rings, sealing rings, and spring contact elements together with at least one holding ring to form a connector having a common bore fore receiving a medical lead cable. Contact grooves for positioning the spring contact elements are formed in part by assembling multiple components together.

23 Claims, 6 Drawing Sheets

U.S. PATENT DOCUMENTS

| | | | |
|---|---|---|---|
| 6,879,857 B2 | 4/2005 | Swanson et al. | |
| 6,895,276 B2 * | 5/2005 | Kast et al. | 607/37 |
| 7,003,351 B2 | 2/2006 | Tvaska et al. | |
| 7,047,077 B2 | 5/2006 | Hansen et al. | |
| 7,062,329 B2 | 6/2006 | Ostroff | |
| 7,063,563 B1 | 6/2006 | Hsu | |
| 7,070,455 B2 * | 7/2006 | Balsells | 439/668 |
| 7,083,474 B1 | 8/2006 | Fleck et al. | |
| 7,108,549 B2 | 9/2006 | Lyu et al. | |
| 7,164,954 B2 | 1/2007 | Lefebvre et al. | |
| 7,187,974 B2 | 3/2007 | Haeg et al. | |
| 7,195,523 B2 | 3/2007 | Naviaux | |
| 7,241,180 B1 | 7/2007 | Rentas Torres | |
| 7,263,401 B2 | 8/2007 | Scott et al. | |
| 7,299,095 B1 | 11/2007 | Barlow et al. | |
| 7,303,422 B2 | 12/2007 | Hoffer et al. | |
| 7,326,083 B2 | 2/2008 | Mehdizadeh et al. | |
| 7,429,199 B2 | 9/2008 | Burgess | |
| 7,601,033 B2 * | 10/2009 | Ries et al. | 439/669 |
| 7,654,843 B2 * | 2/2010 | Olson et al. | 439/248 |
| 7,822,477 B2 * | 10/2010 | Rey et al. | 607/37 |
| 2003/0163171 A1 | 8/2003 | Kast et al. | |
| 2004/0068313 A1 | 4/2004 | Jenney et al. | |
| 2004/0078070 A1 | 4/2004 | Baudino | |
| 2006/0166563 A1 | 7/2006 | Osypka | |
| 2006/0224208 A1 | 10/2006 | Naviaux | |
| 2008/0208278 A1 * | 8/2008 | Janzig et al. | 607/37 |
| 2008/0246231 A1 * | 10/2008 | Sjostedt et al. | 277/641 |
| 2008/0255631 A1 * | 10/2008 | Sjostedt et al. | 607/37 |
| 2009/0258519 A1 * | 10/2009 | Dilmaghanian et al. | 439/271 |

OTHER PUBLICATIONS

Extended European Search Report mailed Oct. 4, 2010 from corresponding European Application No. 08745522.6, filed Sep. 18, 2009 (7 pages).

International Search Report completed and mailed Oct. 7, 2008 from corresponding PCT Application No. PCT/US2008/059924, filed Apr. 10, 2008 (6 pages).

Written Opinion completed and mailed Oct. 7, 2008 from corresponding PCT Application No. PCT/US2008/059924, filed Apr. 10, 2008 (4 pages).

* cited by examiner

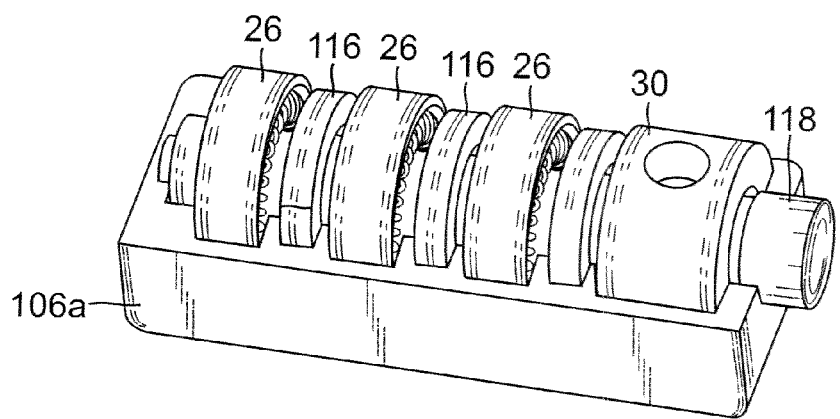
FIG. 9
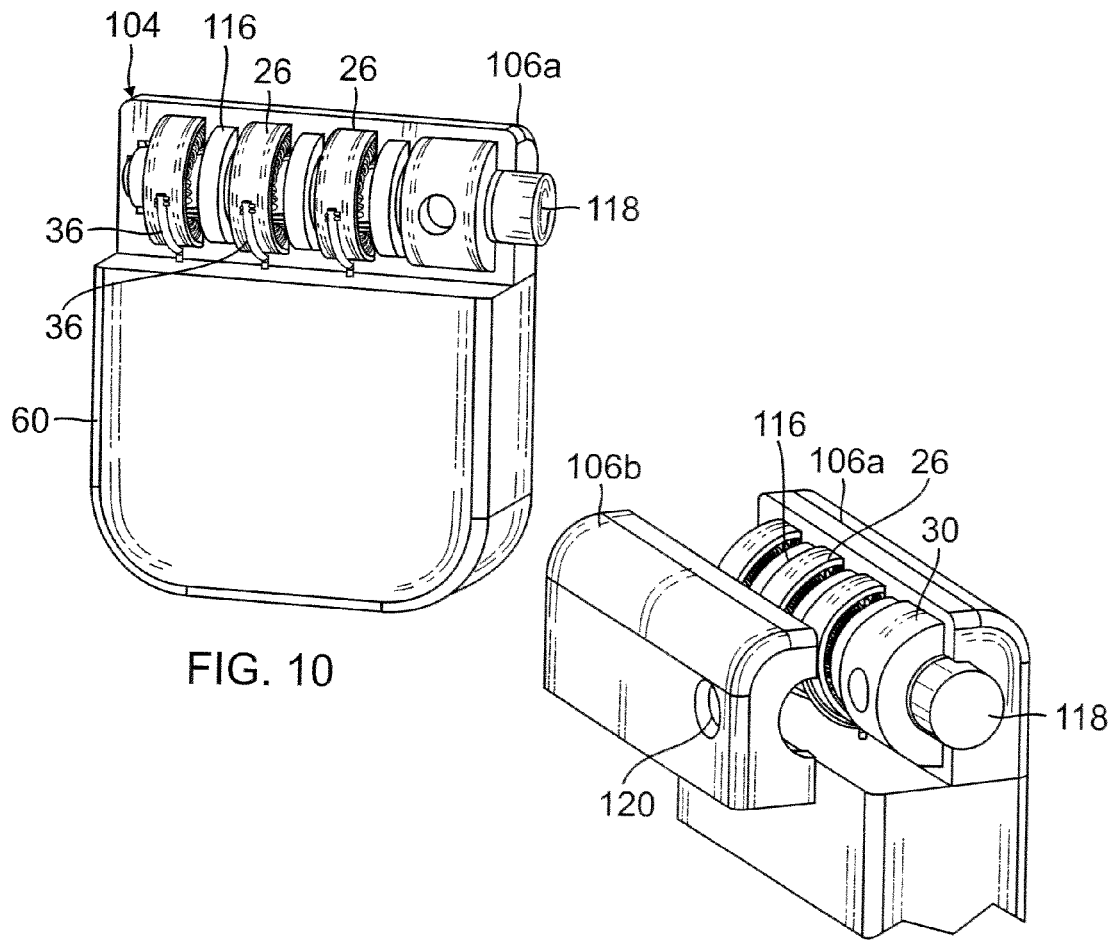
FIG. 10
FIG. 11

INTEGRATED HEADER CONNECTOR SYSTEM

CROSS-REFERENCE TO RELATED APPLICATIONS

This is an ordinary application claiming priority to provisional application No. 60/911,161, filed Apr. 11, 2007, entitled Integrated Header Connector System; and of provisional application No. 61/024,660, filed Jan. 30, 2008, entitled In-Line Connectors; the contents of each of which are expressly incorporated herein by reference as if set forth in full. This application also expressly incorporates by reference application Ser. No. 12/062,895, filed Apr. 4, 2008, entitled Connector Assembly for Use with Medical Devices.

A connector assembly having one or more conductive elements in spaced-apart configuration is generally discussed herein with particular discussions extended to connector assemblies for use with implantable medical devices having easy to assemble contact elements.

BACKGROUND

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neurostimulator pulse generators, which are collectively herein referred to as "implantable medical devices" or IMDs. These IMDs typically incorporate a hermetically sealed device enclosing a power source and electronic circuitry. Connected to the sealed housing, also known as a "can", is a header assembly. The header assembly includes electrical contact elements that are electrically coupled to the electronic circuits or to the power source located inside the can via conductive terminals. The header assembly provides a means for electrically communicating via an external medical lead cable, between the electronic circuits or power source located inside the device and the actual stimulation point.

Industry wide standards have been adopted for, among other things, the dimensions, size, pin spacing, diameter, etc. for the receptacle and the medical lead cable. Furthermore, good electrical contact must be maintained during the life of the implantable medical device, and the medical lead cable for use with the IMD must not disconnect from the receptacle located in the header, yet be detachable for implanting and programming purposes and for replacing the IMD when necessary.

Although prior art connector contacts provide viable options for medical device manufacturers, the overall dimensions of existing receptacles pose manufacturing challenges. Among other things, placing stackable rings in between electrically insulating seals and positioning conductive contact elements in between conductive grooves for forming a receptacle and integrating the contact assembly into the IMD are difficult, costly, and time consuming. Accordingly, there is a need for a receptacle that not only meets the challenges associated with implantable applications but is also easier to manufacture than a variety of existing receptacles. There is also a need for a receptacle that is easily adaptable with existing implantable medical devices that are easier to manufacture than a variety of existing implantable medical devices.

SUMMARY

An aspect of the present invention includes an implantable medical device comprising a header attached to a sealed housing; a connector stack disposed in the header, said header comprising at least two header housing sections attached to one another along a seam. A plurality of grooves are disposed in the at least two header housing sections and a plurality of dividing walls each separating two adjacent grooves from one another. A conductive contact ring element having a spring contact element disposed therein is positioned in a first groove and a sealing ring is positioned in a second groove adjacent the conductive contact ring element and having the dividing wall positioned therebetween for maintaining the conductive contact ring element and the sealing ring in a spaced apart relationship.

Aspects of the present invention also include a method of assembling a connector assembly for use with an implantable medical device. In accordance with on method, the steps comprise providing a first header section comprising a plurality of grooves; placing a conductive contact ring element into a first groove; placing a sealing ring into a second groove; separating the contact ring from the sealing ring with a dividing wall; and attaching a second header section to the first header section.

Another aspect of the present invention is a method for forming a connector stack having reduced overall length comprising inserting a tubular ring into a groove of a header, said groove located between two seal ring elements, to form a ring groove; providing a spring in said ring groove; and maintaining a space between said tubular ring and said two seal ring elements.

In other embodiments, a method is provided for assembling an implantable medical connector stack comprising a series of selecting and dropping steps. The method comprises selecting a first stack component for assembly; dropping the first stack component into a header section; selecting a second stack component for assembly; dropping the second stack component into the header section; and providing a dividing wall, formed of a material different from the first stack component and the second component, in between the first stack component and the second stack component to maintain the first stack component and the second stack component in a spaced apart relationship.

BRIEF DESCRIPTION OF THE DRAWINGS

FIG. 9 is an isometric view of the connector assembly of FIG. 5 assembled in the pre-molded header assembly housing.

FIG. 10 is an isometric view of the IMD of FIG. 5 with part of the header housing removed for clarity.

FIG. 11 is an isometric view of the IMD of FIG. 5 in a different perspective and with part of the header housing being displaced to show how the header housing may be assembled.

Other aspects and features of the receptacles provided herein may be better appreciated as the same become better understood with reference to the specification and claims.

DETAILED DESCRIPTION

The detailed description set forth below in connection with the appended drawings is intended as a description of the presently preferred embodiments of connector assemblies or stacks for electrically communicating with medical leads or conductive terminals. The leads in turn connect to integrated circuits, a power source, and/or circuit chips located inside a sealed medical implantable housing. The connector assemblies provided in accordance with aspects of the present invention are not intended to represent the only forms in which the present invention may be constructed or utilized. The description sets forth the features and the steps for constructing and using the connector assemblies of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein. As denoted elsewhere herein, like element numbers are intended to indicate like or similar elements or features.

Figure 1:
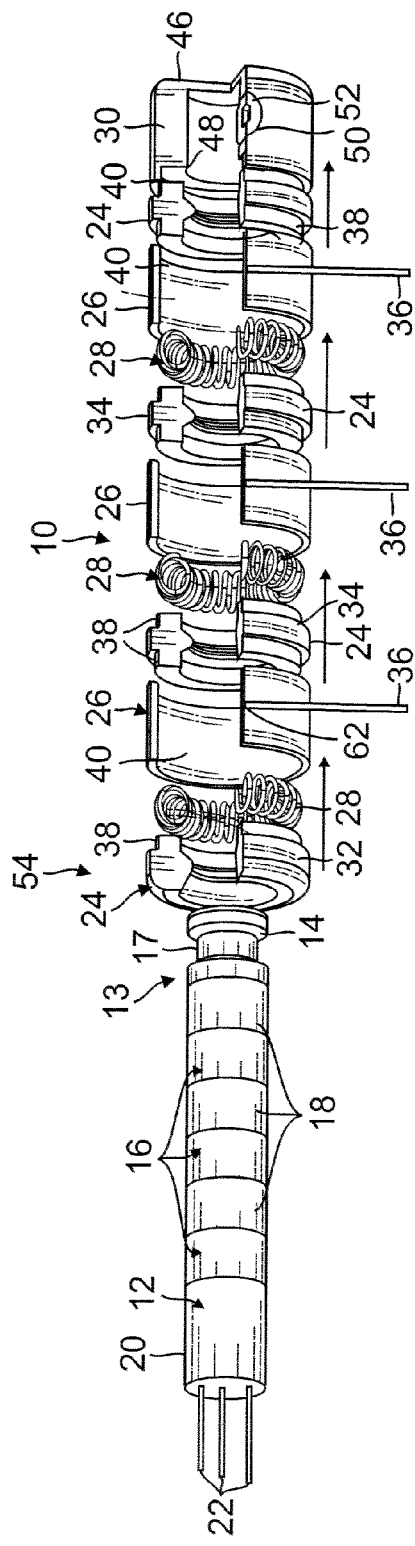
FIG. 1 is an exploded isometric cut-away view of a connector assembly provided in accordance with aspects of the present invention, which comprises a plurality of seal rings, contact rings, and spring contact elements.

Referring now to FIG. 1, an exploded isometric cut-away view of a connector assembly or implantable medical connector stack provided in accordance with aspects of the present invention is shown, which is generally designated 10. The connector assembly 10 is configured to receive a medical lead cable 12, which has a proximal end 13 comprising a proximal tip 14, having a recessed section or groove 17 for accepting a set screw or other lead locking device, and a plurality of electrical terminals 16 interposed in between lead insulators 18. The lead cable 12 further comprises a lead body 20 for carrying a plurality of electrode leads 22 from between the proximal end 13 and a distal end (not shown), which has electrode terminals for providing electrical stimulation to the body tissues. The number of electrode leads 22 and corresponding number of electrical terminals 16 can vary depending on the particular implant application, which also determines the number of electrical ring contacts in the connector assembly 10, as further discussed below. Accordingly, applications of the connector assemblies discussed herein include unipolar, bipolar, and multi-polar applications by simply changing the number of components used to make the connector assembly.

In one exemplary embodiment, the connector assembly 10 comprises a plurality of non-conductive seal rings 24, conductive ring contact elements 26, and spring contact elements 28. Together with a holding ring 30, the plurality of seal rings 24, ring contact elements 26, and spring contact elements 28 form the basic components of the connector assembly 10 of the present embodiment, which has a common bore for receiving the proximal end of the lead cable 12. Broadly speaking, the seal rings 24 are each configured to seal, along its internal diameter, against the lead cable 12 and, along the outer periphery of its exterior shoulders, adjacent ring contact element(s) 26. As is readily apparent to a person of ordinary skill in the art, bodily fluids should be prevented from traveling along the lead cable 12 into the connector assembly or in through the seams between the contact ring element 26 and two adjacent seal rings 24. The ring contact elements 26 are each configured to pass an electric signal from a lead 36 located inside an IMD housing to a corresponding spring contact element 28, which then passes the electric signal to a corresponding electrical terminal 16 on the lead cable 12 then onto a corresponding electrode lead 22 located inside the lead body 20 and to a corresponding electrode terminal on the distal end of the lead cable.

In accordance with aspects of the present invention, two sub-classes of seal rings 24 are incorporated, which include an end seal ring 32 and an intermediate seal ring 34. The end seal ring 32 comprises a single external shoulder 38 for projecting into an adjacent bore 40, which could be that of a contact ring 28 or otherwise. The intermediate seal ring 34 comprises two external shoulders 38 for projecting into two adjacent bores 40, which could be that of two different contact rings 28 or otherwise, such as one contact ring 28 and a holding ring 30. However, an intermediate seal ring 34 can be used in place of an end seal ring 32 without deviating form the spirit and scope of the present invention.

Figure 2:
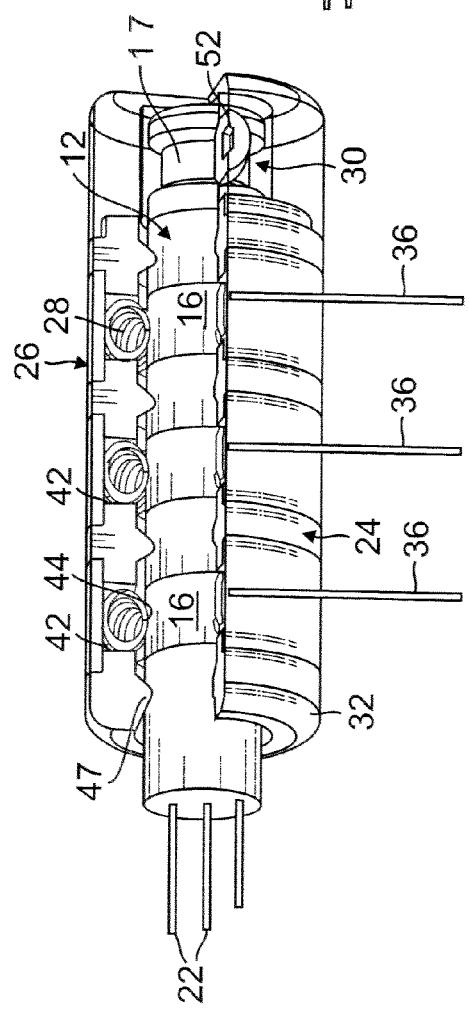
FIG. 2 is an isometric cut-away view of the connector assembly of FIG. 1 in an assembled state with a medical lead cable disposed in the connector bore.

With reference to FIG. 2 in addition to FIG. 1, when two adjacent seal rings 24 engage the bore 40 of a common contact ring element 28, a contact groove 42 is formed for accommodating a spring contact element 28. The spring contact element 28, which is preferably a radial or axial canted coil spring commercially available from Bal Seal Engineering of Foothill Ranch, Calif., is sized so that it is positioned by the groove along its two axial ends and establishes contact along its outer and inner radial circumference. Its internal diameter 44 is preferably smaller than the internal diameter 46 of the seal ring 24, which is slightly smaller than the outer diameter of the proximal end 13 of the lead cable 12. In other words, when the proximal end 13 of the lead cable 12 is inserted into the common bore, the lead cable has a slight interference fit with the plurality of seal rings 24 and the canted coil spring. The seal rings 24 are also in interference fit with the adjacent bores along their respective external shoulders 38 to facilitate assembly of the various components.

The spring contacts 28 are similarly sized so that each is deflected by the lead cable 12 to about 5% and up to about 50% of its total radial deflection with up to about 40% being more preferred. This deflection range ensures a sufficient spring contact force is generated between the contract rings 26 and the electric terminals 16 on the lead cable 12 for transferring electric signals between the two.

Referring again to FIG. 1, in one exemplary embodiment, the contact rings 26 are each generally cylindrical in configuration. More preferably, each contact ring 26 has a generally constant inner diameter and outer diameter with two square ends, with normal manufacturing tolerance being acceptable. Said differently, the contact rings 26 do not have machined or formed grooves for forming contact grooves therein for accommodating the spring contact elements 28. The contact rings 26 have a simple profile, which in one embodiment is tubular in shape and makes manufacturing the rings and assembling the spring contacts 28 therein easier and therefore more cost effective. The contact grooves are formed instead by a combination of adjacent seal rings 24 and the inner surface of the ring contact element 26. While FIG. 1 is the more preferred design, alternative contact ring internal geometries are possible in the area of contact with the spring without compromising ease of assembly for the spring 28 and contact ring. For example, the contact ring inside diameter can have a "v" shaped groove geometry in the area of the spring contact so that two points of contact are available with the spring versus one.

Other geometries are also contemplated. For example, the contact ring 26 may have a thicker section so that there are at least two internal diameters. The spring contact element 28 can then be inserted through the larger internal diameter end of the contact ring 26 until it abuts the shoulder formed at the intersection between the two different internal diameters. Thus, different diameters and undulating internal surfaces for the contact rings are contemplated. The ring with a v-shaped groove can be considered a sub-species of a ring having at least two internal diameters. Still alternatively, the plurality of contact rings in a single connector assembly may vary, i.e., are not uniform. For example, it is possible to use a ring with a "v" shaped groove at the distal most end of the connector assembly and rings with a smoother contour as shown in FIG. 1 for the remaining contact rings. Still alternatively, a ring with two different internal diameters may be used with the ring having a v-shaped groove and with rings having a uniform internal diameter. If a contact ring having two different internal diameters at its two ends is used, the seal rings 24 are modified accordingly to engage the different internal diameters of the contact ring. Thus, contact rings provided herein not only can have a smooth internal diameter, but also machined surfaces and undulating surfaces.

Thus, in accordance with one aspect of the present invention, there is provided a method for assembling a plurality of components to form a connector assembly comprising engaging a first seal ring 34 to a holding ring 30, engaging a first contact ring 26 with the first seal ring 34, placing a first spring contact element 28 inside the first contact ring, and engaging a second seal ring 34 with the first contact ring to form a ring groove for constraining the first spring contact therein. The method further comprises the steps that include adding other seal rings, contact rings, and spring contact elements to form a connector assembly having a desired number of contact grooves. More preferably, the method further comprises the steps of assembling a connector assembly without having to utilize a tool or by hand or by secondary assembly processes manipulate, compress, bend, or distort a spring contact to fit within a contact groove. The assembled connector assembly is then placed into a mold cavity and over-molded with an implantable grade polymer or elastomer, such as epoxy or silicone. The connector assembly can also be inserted into a pre-molded header, which resembles a housing having a cavity for receiving the connector assembly and one or more openings for placing the connector assembly into the pre-molded header. The one or more openings are then backfilled or sealed, typically after attaching or welding the leads from the sealed housing to the contact rings, to complete the assembly.

In accordance with other aspects of the present invention, there is provided an alternative method for assembling a connector assembly in which a dowel or assembly pin (not shown) is used, which resembles the proximal end 13 of the lead cable 12 shown in FIG. 1. The assembly pin (not shown) is used to construct the connector assembly 10 by first placing a holding ring 30 on an end of the assembly pin and then subsequently placing other components on the pin and then sliding them into engaging with the earlier placed components. The assembled components, i.e., the connector assembly, may then be secured by placing the same inside a cavity and over-molding the assembly with an implantable grade polymer or elastomer.

In the embodiment shown, the holding ring 30 functions as an end cap and has an end wall 46 and a shoulder 48 for mating engagement with the shoulder on the seal ring 34. However, a reverse configuration in which the holding ring 30, or contact ring 26, projects into the seal ring 24 is envisioned, although less preferred. A threaded bore 50 for receiving a set screw 52 is incorporated in the holding ring 30 to more securely fixing the lead cable 12 to the connector 10 assembly (FIG. 2). Alternatively, an end holding ring (not shown) may be incorporated at the distal most end 54 of the connector assembly for providing the locking function on the lead cable 12. During the over-molding step, a window should be formed around the threaded bore 50 for securing the lead cable, which can then be back-filled using a curable and implantable material.

Referring again to FIG. 2, the seal rings 24 of the present embodiment, except for the end seal ring 32, are each symmetrical abound a centerline drawn perpendicular to the axis defined by the lead cable 12 and through the center of the seal ring. However, non-symmetry or other configurations are possible so long as a contact groove for accommodating a spring contact is formed at least in part by engaging the contact ring 26 with two adjacent seal rings 24. Furthermore, while the seal rings 24 of the present embodiment are shown each comprising an internal projection for sealing against the lead cable 12, as previously discussed, two or more projections may be incorporated without deviating from the spirit and scope of the present invention. Still furthermore, part of the seal ring that projects into the bore of a contact ring can be made separately. In other words, a seal ring may be made by co-molding over over-molding two separate components.

Following assembly of the various components to form the connector assembly 10 shown in FIG. 2, the connector assembly is encased inside an implantable elastomer or polymer layer, as previously discussed. The connector assembly 10 is preferably molded with an assembly pin located inside the common bore to ensure alignment, both radially and axially, of the various connector components. The encased connector may be referred to as a connector header, for placing on a can or sealed housing of an IMD. In one exemplary embodiment, windows (not shown) are left exposed through the over-molded layer adjacent each contact ring 26. When the header is placed over the can, a plurality of contact leads 35 in communication with a power source and/or electronic circuits inside the can project upwardly into physical contact with the contact rings 26. The contact leads 36 may then welded to a corresponding contact ring 26 to ensure good electrical contact through the windows. The windows are then backfilled and sealed using curable implantable elastomer or polymer.

Figure 3:
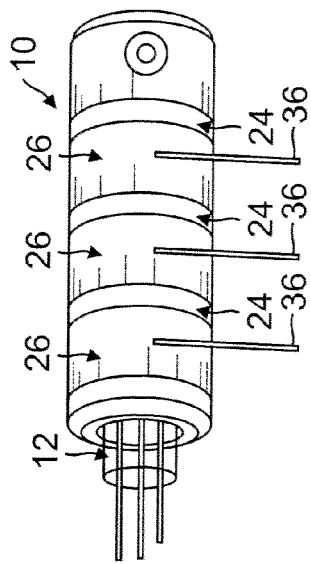
FIG. 3 is an isometric view of the connector assembly of FIG. 2.

FIG. 3 is fully assembled view of the connector assembly 10 of FIGS. 1 and 2 with the medical lead cable 12 disposed inside the common bore. As can be appreciated, the connector stack 10 provided herein allows for the distance between one ring contact element and an adjacent ring contact element to be reduced. The reduction is facilitated by, among other things, eliminating metallic side walls for capturing the springs inside the ring grooves. Thus, the overall length of the stack, from the holding ring 30 to the distal end most seal element 24, may be reduced compared to connector stacks having metallic or conductive side walls for capturing the springs. Accordingly, a method is provided for forming a connector stack having reduced overall length comprising inserting a tubular ring into a groove between two seal ring elements to form a ring groove, and providing a spring in said ring groove. Advantageously, the stack provided in accordance with aspects of the present invention reduces manufacturing and installation costs, simplifies assembly, and shortens the overall length of the stack to allow for smaller sized IMDs.

Figure 4:
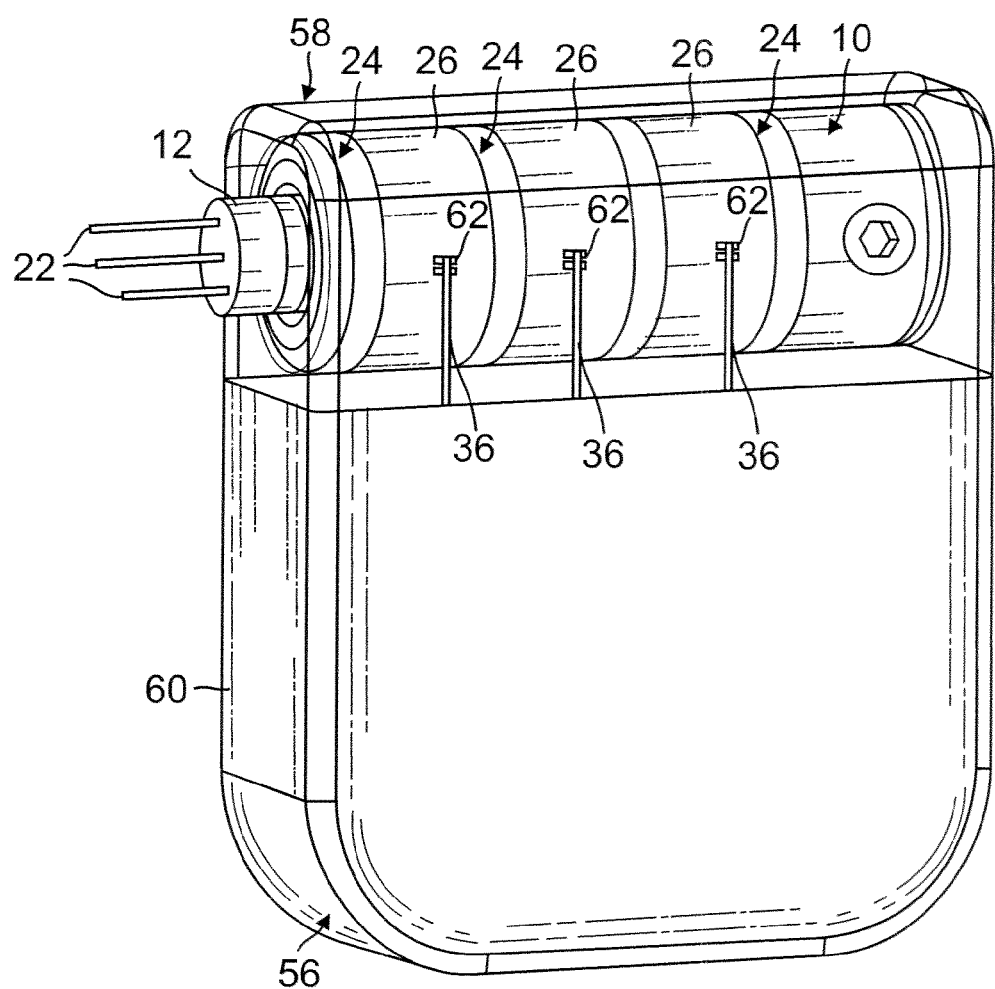
FIG. 4 is an isometric transparent view of the connector assembly of FIGS. 1-3 inside a header and atop a sealed housing of an implantable medical device.

Referring now to FIG. 4, an IMD 56 incorporating a connector assembly 10 provided in accordance with aspects of the present invention is shown. The connector assembly 10 is shown in a header 58, which is shown as a transparent material or structure for purposes of discussion. In practice, the overcoat or over-molding layer is more commonly semi-opaque. The header 58 is situated over a can 60, which is hermetically sealed with a power source, electronic circuits. As previously discussed, the IMD can be any one of plurality of IMDs for medical treatment, monitoring, or diagnostics.

Also shown in FIG. 4 are weld traces 62 for welding the leads 36 to the contact rings 26. Typically, the leads 36 project through one or more feed through terminals that pass through the hermetically sealed housing or can 60 to contact the contact rings 26. Although a single connector assembly 10 is shown inside the header 58, two or more connector assemblies 10 may be used if desired depending on the particular implant application. The connector assemblies may be stacked side-by-side or on top of one another.

Figure 5:
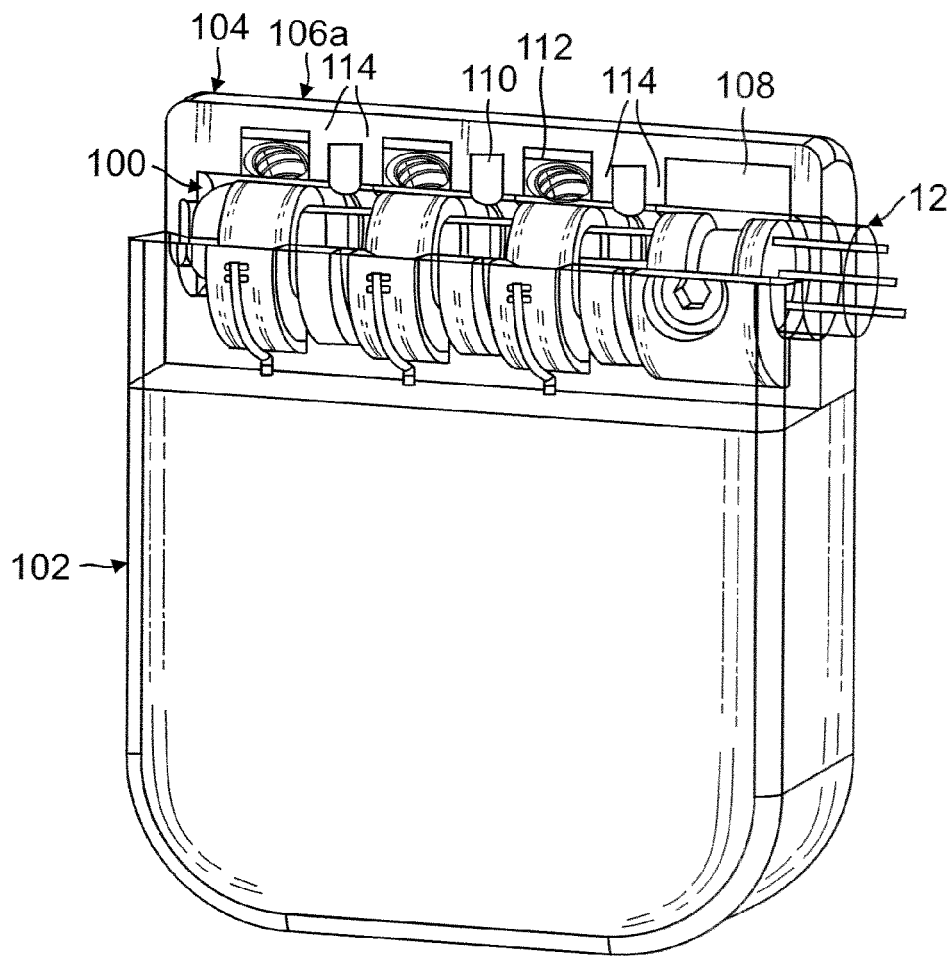
FIG. 5 is an isometric cut-away transparent view of an alternative connector assembly provided in accordance with aspects of the present invention usable with an IMD.

FIG. 5 is a an isometric cut-away transparent view of an alternative connector assembly 100 provided in accordance with aspects of the present invention for use with an IMD 102. The present connector assembly 100 is configured to be assembled to a pre-formed header housing 104. In one aspect of the present invention, the header housing 104 comprises two housing sections 106a, 106b each formed with a plurality of cavities or grooves 108, 110, 112. The grooves are each spaced apart from one another by a dividing wall 114. Furthermore, each groove is configured to accommodate or accept a specific connector component. Accordingly, there is provided a holding ring groove 108, a sealing ring groove 110, and a contact ring groove 112.

The grooves are each sized to snuggly receive a connector component. Moreover, they are sized and aligned so that when the various connector components are mounted therein, the bores of the various components align. More preferably, the grooves are aligned to provide a generally uniform longitudinal axis among the various connector components to define a common bore.

Figure 6:
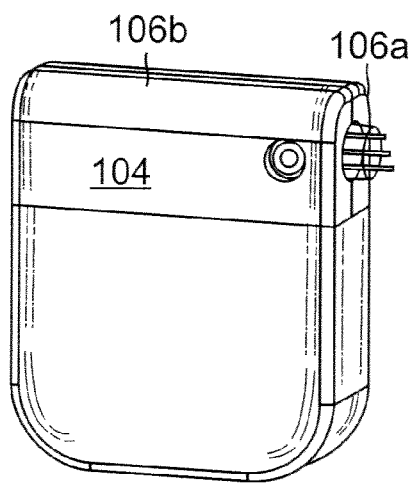
FIG. 6 is an isometric view of the alternative connector assembly of FIG. 5.

FIG. 6 is an isometric view of the alternative connector assembly of FIG. 5 in a fully assembled position. As can be appreciated, the connector stack 100 provided herein allows for select and drop installation. That is, the connector stack 100 may be assembled by pick and choosing the proper component and dropping that component into a proper groove. For example, a ring and spring combination will be dropped into a contact ring groove and a sealing ring element is to be dropped into a sealing ring groove to assemble the stack. Accordingly, a method is provided for assembling an implantable medical connector stack comprising selecting a first stack component for assembly; dropping the first stack component into a header section; selecting a second stack component for assembly; dropping the second stack component into the header section; and providing a wall, formed of a material different from the first stack component and the second component, in between the first stack component and the second stack component to maintain the first stack component and the second stack component in a spaced apart relationship. In another aspect of the present invention, a canted coil spring is placed inside the first stack component or the second stack component before placement of said stack component into the header section. In another embodiment, the wall is singularly formed with the header section, preferably made from an polymer or elastomer material, such as epoxy or silicone.

Figure 7:
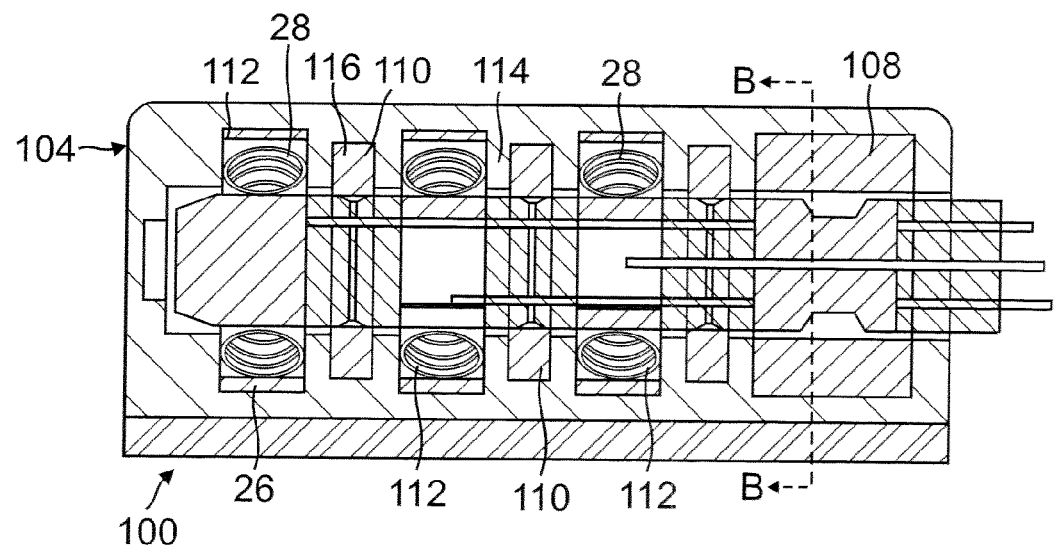
FIG. 7 is a cross-sectional side view of the header assembly of the connector assembly of FIG. 5.

FIG. 7 is a cross-sectional side view of the connector assembly 100 located inside the header housing 104. As shown, a first contact ring 26, having a spring contact element 28 positioned therein, is positioned in a first groove 112. A sealing ring 104 is positioned in a second groove 110. A second contact ring 26 and spring contact element 28 are positioned in a third groove 112. A second sealing ring 116 is positioned in a fourth groove 110 and so forth. The connector assembly 100 may have as few as one contact ring 26 and as many as necessary to perform the needed tasks for a particular IMD application. In the embodiment shown, a third contact ring 26 having a spring contact element 28 is positioned in a fifth groove 112. A holding ring 30 comprising a threaded bore for cooperating with a set screw is positioned in the seventh groove 108. In one embodiment, the outside diameter (OD) of the sealing ring 116 and the OD of the ring contact element 26 is about the same. More preferably, the OD of the sealing ring 116 is smaller than the OD of the ring contact element 26.

As can be appreciated, a feature of the present embodiment is a plurality of header walls 114 located in between alternating pairs of ring contact elements 26 and sealing rings 116 to keep the stack components in spaced apart relationships, except for the springs 28 and the ring contact elements 26, which are always in electrical communication with one another. In another aspect of the invention, a method is provided for forming ring grooves for retaining canted coil springs in the absence of conductive side walls. The method comprising placing a first ring contact element into a first groove of a header and forming a ring groove from a bottom wall of the ring contact element and two header walls. The method further comprising placing a dielectric seal element into a second groove, spaced apart from the first groove, and placing a second ring contact element into a third groove, which is spaced apart from the second groove and the first groove.

As is readily apparent to a person of ordinary skill in the art, each contact ring 26 is isolated from an adjacent contact ring by a sealing ring 116 and at least one dividing wall 114. The sealing rings are each preferably generally ring shape (FIG. 8) and comprises a bevel inner circumference or opening for sealing engagement with a medical lead cable.

Figure 8:
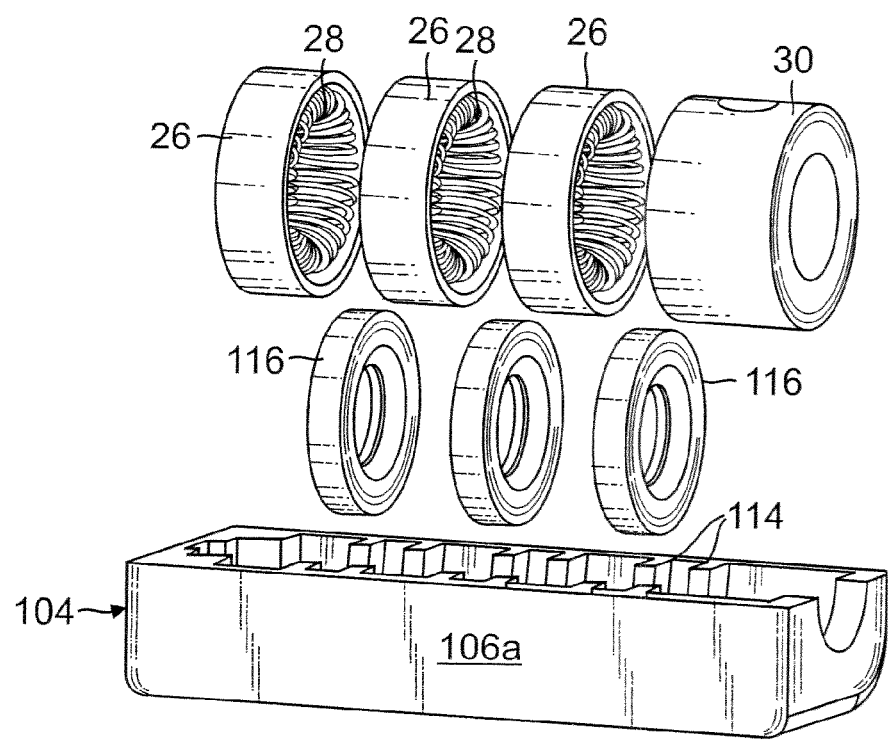
FIG. 8 is an exploded isometric view of the header assembly of the connector assembly of FIG. 5 with part of the header housing removed for clarity.

FIG. 8 is an exploded isometric view of the header assembly or stack 100 of FIG. 5 with part of the header housing 104 removed for clarity. The connector assembly may be assembled into a header housing 104 by first inserting the various connector components into the plurality of grooves inside a first housing section 106a. As discussed above, the grooves are pre-formed into the two housing sections 106a, 106b. The embodiment shown allows for easy installation by simply inserting the plurality of connector components or stack components, i.e., ring contact elements, seal ring elements, canted coil springs, and one or more holding rings, into a matching groove, i.e., having matching dimensions and/or geometries for accommodating the corresponding stack components. To provide for more accurate alignment, an assembly pin 118 (FIG. 9) is preferably inserted into the common or aligned bore before coupling the second housing section 106b with the first housing section, which are then glued or bonded together using any known prior art methods. In an alternative embodiment, a plurality of windows may be provided in the two housing sections 106a, 106b to back-fill with curable implantable elastomer or polymer to maintain alignment. The curable material flows into the crevices to hold the various components in alignment even after the assembly pin is removed.

FIG. 10 is an isometric view of the IMD of FIG. 5 with part of the header housing 104 removed for clarity. As shown, contact leads 36 from the sealed housing 60 are welded to the contact rings 26 prior to coupling the second housing section 106b with the first housing section 106a (FIG. 11). A window 120, which can be back-filled with curable material, is provided for manipulating a set screw. In one aspect of the present invention, a beveled section may be provided along the seam of the two housing sections 106a, 106b for facilitating assembly of the two housing sections.

Figure 12:
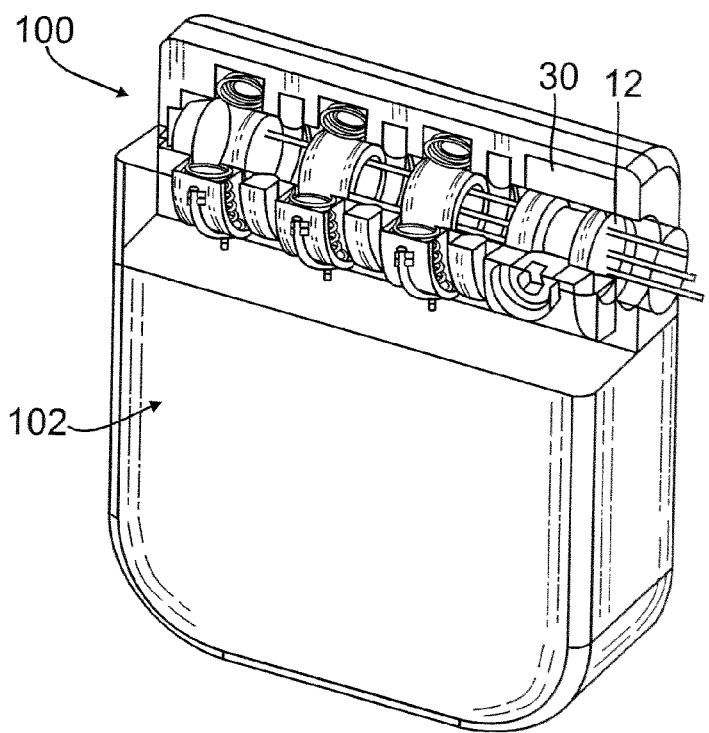
FIG. 12 is an isometric view of the IMD of FIG. 5 in a different perspective.

FIG. 12 is an isometric view of the IMD of FIG. 5 in a different perspective. FIG. 12 shows the assembly pin removed and a medical lead cable 12 coupled to the connector assembly.

Figure 13:
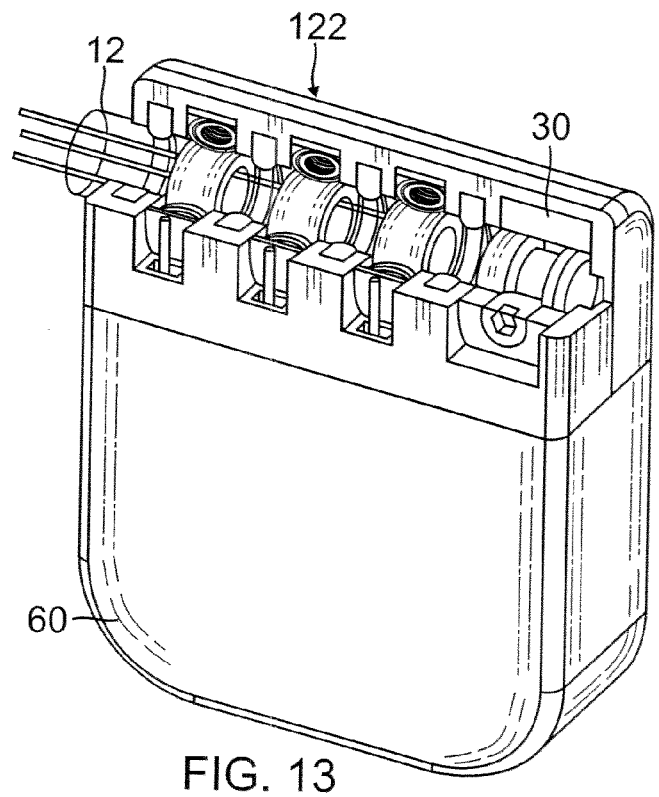
FIG. 13 is an isometric view of yet another alternative connector assembly provided in accordance with aspects of the present invention used with an IMD.

FIG. 13 is a isometric view of yet another alternative connector assembly 122 provided in accordance with aspects of the present invention for use with an IMD. In the present alternative connector assembly 122, the holding ring 30 has been moved to the proximal end of the connector assembly.

Although limited preferred embodiments and methods for making and using connector assemblies provided in accordance with aspects of the present invention have been specifically described and illustrated, many modifications and variations will be apparent to those skilled in the art. For example, various material changes may be used, incorporating different mechanical engagement means to attach the various components to one another, making use of two or more different materials or composites, making a sealing ring from multiple pieces rather than a singularly molded piece, etc. Accordingly, it is to be understood that the connector assemblies constructed according to principles of this invention may be embodied in other than as specifically described herein. The invention is also defined in the following claims.

What is claimed is:

1. A method of assembling a connector assembly for use with an implantable medical device comprising:
    providing a header with a first header section and a second header section separated from one another along a lengthwise seam; the first header section and the second header section comprising a same number of grooves;
    placing a conductive contact ring element with a spring contact element into a first groove;
    placing a sealing ring into a second groove;
    separating the contact ring from the sealing ring with a dividing wall; and
    attaching a second header section to the first header section.

2. The method of claim 1, further comprising placing a second conductive contact ring element into a third groove, which is spaced apart from the second groove and the first groove before attaching the second header section to the first header section.

3. The method of claim 2, wherein the spring contact element is a radial canted coil spring.

4. The method of claim 3, further comprising placing a second sealing ring into a fourth groove before attaching the second header section to the first header section.

5. The method of claim 1, further comprising placing an assembly rod in through the conductive ring contact element before placing the conductive ring contact element into the first groove.

6. The method of claim 1, wherein the dividing wall is singularly formed with the first header section.

7. The method claim 6, wherein the second header section comprises a plurality singularly formed dividing walls.

8. A method is provided for assembling an implantable medical connector stack comprising selecting a first stack component for assembly;
    dropping the first stack component into a first groove of a header section;
    selecting a second stack component for assembly;
    dropping the second stack component into a second groove of the header section; and
    providing a dividing wall, formed of a material different from the first stack component and the second component, in between the first stack component and the second stack component to maintain the first stack component and the second stack component in a spaced apart relationship; and
    wherein a spring contact element is located with the first stack component or the second stack component.

9. The method of claim 8, further comprising dropping a holding ring into a groove of the header section.

10. The method of claim 8, further comprising attaching a second header section to the header section.

11. The method of claim 10, further comprising attaching the header section and the second header section to a sealed housing of an implantable medical device.

12. A method of assembling a connector assembly for use with an implantable medical device comprising:
    providing a header with a first header section and a second header section; the first header section comprising a plurality of grooves;
    placing a conductive contact ring element with a spring contact element into a first groove;
    placing a sealing ring into a second groove;
    separating the contact ring from the sealing ring with a dividing wall; and
    attaching a second header section to the first header section;
    wherein the first header section and the second header section define a lengthwise seam extending from a first end of the header to a second end of the header with a receiving bore for receiving a lead located at the first end or the second end.

13. The method of claim 12, wherein the first header section and the second header section comprise a same number of grooves.

14. The method of claim 12, further comprising placing a second conductive contact ring element into a third groove, which is spaced apart from the second groove and the first groove before attaching the second header section to the first header section.

15. The method of claim 14, wherein the spring contact element is a radial canted coil spring.

16. The method of claim 15, further comprising placing a second sealing ring into a fourth groove before attaching the second header section to the first header section.

17. The method of claim 12, further comprising placing an assembly rod in through the conductive ring contact element before placing the conductive ring contact element into the first groove.

18. The method of claim 12, wherein the dividing wall is singularly formed to the first header section and is made from a non-conductive material.

19. A method for forming a connector stack having reduced overall length comprising inserting a tubular ring into a groove of a header, said groove located between two seal ring elements, to form a ring groove; providing a spring in said tubular ring; and maintaining a space between said tubular ring and said two seal ring elements.

20. The method of claim 19, wherein said tubular ring has a bottom wall and no side walls.

21. The method of claim 19, further comprising placing a second tubular ring into a groove located adjacent one of the two seal ring elements.

22. The method of claim 21, wherein the second tubular ring is separated from one of the two seal ring elements by a dividing wall.

23. The method of claim 19, further comprising placing a holding ring into a groove.

* * * * *